United States Patent [19]

King et al.

[11] Patent Number: 5,481,903
[45] Date of Patent: Jan. 9, 1996

[54] METHOD AND INSTRUMENT FOR VISCOELASTIC MEASUREMENTS

[75] Inventors: David King, Lechlade; Michael Stolc, Swindon; David Rusling, Swindon, all of United Kingdom

[73] Assignee: Monsanto plc, Basingstoke, United Kingdom

[21] Appl. No.: 335,289

[22] Filed: Nov. 7, 1994

[30]        Foreign Application Priority Data

Nov. 15, 1993 [GB] United Kingdom ............... 9323544

[51] Int. Cl.⁶ ................................................. G01N 11/10
[52] U.S. Cl. ........................................ 73/54.28; 73/54.16
[58] Field of Search ........................... 73/54.23, 54.28, 73/54.31, 54.32, 54.22, 54.16

[56]              References Cited

U.S. PATENT DOCUMENTS

| 2,074,174 | 3/1937 | Goodier | 73/54.28 |
|---|---|---|---|
| 2,427,796 | 9/1947 | MacDonald | 73/54.28 |
| 2,801,537 | 8/1957 | Kabelitz | 73/54.22 |
| 3,307,619 | 3/1967 | Kim . | |
| 3,407,618 | 10/1968 | Mullins, Jr. | 73/54.28 |
| 3,488,992 | 1/1970 | Veith et al. | 73/15.6 |
| 3,531,996 | 10/1970 | Harris et al. . | |
| 3,534,594 | 10/1970 | Westlinning et al. | 73/101 |
| 3,535,914 | 10/1970 | Ueith et al. . | |
| 3,538,758 | 11/1970 | Karper et al. | 73/54.28 |
| 3,722,262 | 3/1973 | Gilinson, Jr. et al. | 73/54.28 |
| 4,176,968 | 12/1979 | Kromer et al. | 73/54.32 |
| 4,535,621 | 8/1985 | Gervais et al. | 73/54.23 |
| 4,539,838 | 9/1985 | Fraleigh | 73/54.23 |
| 4,546,438 | 10/1985 | Prewittt et al. | 73/54.31 |
| 4,552,025 | 11/1985 | Barker et al. | 73/846 |
| 4,584,882 | 4/1986 | Tosaki | 73/847 |
| 4,736,593 | 4/1988 | Williams | 73/54.32 |
| 4,794,788 | 1/1989 | Masters et al. | 73/59 |

FOREIGN PATENT DOCUMENTS

| 0043892 | 4/1981 | European Pat. Off. . |
|---|---|---|
| 3636872 | 5/1988 | Germany . |

*Primary Examiner*—Richard Chilcot
*Assistant Examiner*—George M. Dombroske
*Attorney, Agent, or Firm*—W. W. Brooks; G. B. Seward

[57]                ABSTRACT

An apparatus for measuring viscoelastic properties of rubbery materials is disclosed. The instrument comprises two opposed dies having temperature and pressure controling means, means for initiating oscillatory rotation of one of the dies whereby the sample is cooled during its residence between the dies and reheated whereby torque measurements are carried out during the period of cooling. A method for operating the claimed apparatus is also disclosed.

11 Claims, 7 Drawing Sheets

METHOD AND INSTRUMENT FOR VISCOELASTIC MEASUREMENTS

This invention relates to a method and an instrument for measuring the viscoelastic properties of rubber and like materials. More particularly, the invention relates to an instrument having two opposed dies adapted to contain between them under pressure a sample of material to be tested, means to apply an oscillatory rotary torque to one of said dies, means for measuring said torque or the torque induced in the other die, and means for deriving information on the properties of the material from such measurements. Examples of such instruments are described in GB-A-1247371, U.S. patent application Ser. No. 4552025 and U.S. patent application Ser. No. 4584882.

Using an essentially sinusoidal oscillatory torque, useful parameters for characterising viscoelastic materials derivable from such measurements are the elastic or storage modulus S', the viscous or loss modulus S" and the tangent of the loss angle (delta) which is the ratio S"/S'. S' can be calculated from the torque measured at maximum displacement, while S" can be calculated from the torque at zero displacement, or alternatively by taking multiple samples of torque during each cycle and extracting S' and S" using Fourier transform calculations as described in European Patent EP-B 0313540.

Such instruments have been developed mainly to monitor the change in properties of vulcanisable rubber compounds during vulcanisation. In a typical test, a sample of the rubber compound is held under pressure between the dies at a fixed temperature appropriate to the rubber under test. As crosslinking of the rubber proceeds during vulcanisation, it is usual for the sample to contract. Such contraction can lead to slippage between the sample and the dies and hence to incorrect values for the torque measurements. The problem is most likely to occur towards and after the end of vulcanisation, and can therefore be serious if information on the behaviour of the rubber at that period is required. The problem can be alleviated by suitable design of the dies. For example, the die system described in U.S. patent application Ser. No. 4552025 has discontinuous annular protrusions, while the dies in a commercial instrument have radial grooves. A proposal for dealing with the problem of slippage is made in CA-A-833240 with reference to a rheometer instrument in which shear is applied to a sample of test material by means of an oscillating rotor embedded in the sample in a pressurised cavity. It is pointed out that in addition to slippage due to crosslinking, slippage can also occur when the temperature of the sample is reduced. The proposal of CA-A-833240 is the provision of a die system wherein at least part of a die is made of material of the proper strength and elasticity to expand under sample loading pressure and to contract after sample loading. However, it has not been considered practicable to apply the idea of the so-called 'diaphragm die' to the type of instrument described in the first paragraph above.

As indicated above, in a typical test using an instrument in the field of the invention, a sample of rubber compound is held under pressure between the dies at a fixed temperature. However, in U.S. patent application Ser. No. 4552025 a test is described in which torque readings are taken with the sample held at a predetermined temperature and when subjected to two or more oscillatory frequencies, and at another, higher predetermined temperature with the sample being subjected to one or more oscillatory frequencies. Cooling of the dies does not appear to have any special significance in the method and apparatus of U.S. patent application Ser. No. 4552025, but it is said that an air blast can be used for cooling and that for quick cooling of the dies an air jet can be positioned so as to reduce their temperature as desired.

We have now found that improved characterisation of viscoelastic materials is achieved by a method in which a sample of material is held under measured pressure and temperature between two opposed, temperature-controlled dies, which method comprises subjecting the sample to an oscillatory rotary shearing force by oscillatory rotation of one of said dies relative to the other and measuring a torque which is indicative of the response of the sample to the shearing force; characterised in that at least once during its residence between the dies the sample is (i) cooled and, if necessary, the resultant pressure drop is limited to avoid slippage between the sample and the dies, and (ii) reheated, and dynamic properties of the sample are derived from the torque measurements at least during the period or periods of cooling.

In a typical procedure when the instrument has upper and lower dies moveable between an open position and a closed position, a sample of the material to the tested is loaded on to the lower die, with the dies in the open position, and the dies are then closed. The dies are held at a temperature at least high enough to soften the material sufficiently for it to mould itself easily and accurately to the shape of the dies during closure. This temperature can, for example, be within the range 70°–200° C. The gap between the dies, ie. the thickness of the moulded sample, is sufficiently small for the entire sample rapidly to assume the temperature of the dies. A short time, generally within 60 seconds, after closure of the dies, cooling is applied. An average rate of cooling of at least 0.3° C. per second is desirable, preferably at least 1° C. per second, for example 2° C. per second. Although useful information can be obtained from torque readings during, say a 20° C. drop in temperature, it is preferred to continue cooling and torque sampling until the temperature of the sample has dropped by at least 50° C. A sample temperature in the range 0°–20° C. at the end of the cooling period is especially preferred. Torque, pressure and temperature readings obtained during this period of cooling can be translated into information on the processing characteristics of the material.

The sample is then reheated, preferably at an average rate of at least 1° C. per second, and cooled again at least once, preferably while continuing to monitor torque, temperature and pressure. The sequence of cooling and reheating can be repeated almost indefinitely if the material is thermoplastic, for example a raw polymer, and any changes in the dynamic properties of the material are likely to occur only slowly. In a preferred procedure for the characterisation of a vulcanisable elastomer composition, there is an initial cooling and reheating stage, as described above, before the onset of vulcanisation. The reheating will raise the temperature of the sample to a level which is appropriate for the elastomer under test, normally a temperature within the range 150°–200° C. Cooling and reheating can, if desired, be repeated once or several times during vulcanisation, but characterisation of the fully vulcanised elastomer composition (complete vulcanisation being indicated by torque at vulcanisation temperature reaching a maximum), is usually the most important. This requires torque, temperature and pressure monitoring to continue during a final cooling of the sample. It is during cooling of a fully vulcanised elastomer sample that slippage between the sample and the dies is most likely to occur and pressure compensation to be required. Slippage can, however, also occur during cooling before the onset of vulcanisation or even with an uncompounded raw polymer. It is especially likely to be evident in procedures where a heat-resistant film is placed between the sample and the dies. This is-sometimes done in the testing of 'sticky' materials which would otherwise stick to the dies, but it is also done in the procedure for automating the testing of samples described in European patent application number (EP-A-0511189) when film is used as a belt to convey samples to and/or from the test position of a test instrument. The critical cavity pressure corresponding to the onset of slippage for a given die configuration will vary according to the particular elastometer compound, whether or not film is used, and to some extent, in the absence of film, on the material from which the dies are made. For SBR compounds cured at 170°–190° C., using toughened steel dies without film, this critical pressure is typically within the range 100–500 psi.

When the sample of viscoelastic material is held under pressure between dies as in the method of the invention, changes in pressure and in the gap between the dies will follow the expansion or shrinkage of the sample as the temperature changes. As the gap increases, the torque signal decreases and vice versa. Results of greater accuracy can be obtained by correcting for this gap-dependent component of the torque; for such correction it is necessary to know the size of the gap corresponding to any given torque reading. A correlation between gap and pressure can be established by a calibration technique as follows using a series of shims of accurately-known thicknesses. The position of one die (normally the lower die) relative to its housing is adjusted so that when the dies and housings are closed under standard closing force, there remains a gap between a reference shim, placed on the lower die, and the upper die. The vertical position of the adjustable die is then moved towards the other die, with the housings remaining closed, until the pressure transducer just senses contact between the upper die and the shim. This gives a reference gap size the same as the thickness of the reference shim and corresponding to essentially zero pressure. The dies and housings are then opened, the reference shim is replaced by the next thicker shim, and the dies and housings are closed using the standard closing force and without further adjustment of the position of the adjustable die. The pressure reading is noted. This sequence is repeated using shims of incremental thicknesses. A plot of pressure against shim thickness (die gap) shows an essentially linear relationship, and a value V for the change in die gap per unit change in pressure can be obtained from the slope of the line. By carrying out this calibration at a series of different die temperatures, it is found the value of V is essentially independent of temperature. The corrected torque is obtained using the value V in the equation:

$$T^*_{corr}=T^*[((pressure \times V)+gap\ ref)/gap\ ref]$$

Where 'gap ref' is the reference gap used in the calibration of the instrument. The description above refers to one die being adjustable for the calibration, but it would in fact be possible to have both dies adjustable relative to their housings.

An extension of the above calibration procedure is required when the pressure drop is limited in the method of the invention to prevent slippage between the sample and the dies. When a sample is rapidly cooled, the pressure decay relative to the temperature is typically of the form illustrated in FIG. 1 of the drawings. In the illustrated case, the limiting pressure has been set to 350 psi and this remains substantially constant below 50° C. It is therefore not possible to rely on the pressure/gap relationship described above in deriving a corrected torque value in this region. In the situation illustrated in FIG. 1, although the pressure remains constant, the die gap continues to close below 50° C. Because the pressure/temperature relationship is substantially linear over the range from about 190° C. to about 75° C. extrapolation of the line below 75° C. can be relied on to give the relationship below that temperature. The relationship over the whole temperature range can be expressed in the form: Pressure=a temp+c where a and c are constants obtained from the illustrated data. From the calibration procedure, the gap (gt) at any given temperature and pressure (p) is given by gt=pV, which from the above pressure/temperature relationship can be written as gt=(a temp+c) v. The corrected torque value is expressed as:

$$T_{corr}=T[(gt+g\ ref)/g\ ref]$$

Where T is the actual complex torque reading at any point during cooling.

In this preferred method the die gap is determined from the pressure/temperature relationship. Alternatively the die gap could be obtained directly from a transducer or sensor that continuously measures the gap at the centre of the dies, eg. on an LVDT or capacitance sensor.

In the method of the invention, a sample of viscoelastic material is subjected to an oscillating, rotary shearing force by oscillatory rotation of one of the dies relative to the other and a torque indicative of the response of the sample to the shearing force is measured. The rotation is preferably essentially sinusoidal through an angle from 0.01 to 10° and at a frequency of from 1 to 10,000 cycles per minute. The torque required to oscillate the said one die can be measured, but alternatively and preferably, the torque induced in the other die is measured.

The raw data from measurements of torque, temperature and pressure are preferably fed to electronic data handling equipment, which can express derived quantities, eg. S' and S", and present them as a visual display or print them on a chart.

In one aspect, the apparatus of the invention for testing a sample of viscoelastic material, comprises two opposing, relatively rotatable dies which are moveable between an open position and a closed position, and which are adapted, when in a closed position, to be separated by a gap and to hold between them a sample under pressure in a cavity defined by the opposing faces of the dies and a peripheral seal, means for heating the dies, means for cooling the dies, means for sensing the temperature of the dies, means for sensing the pressure in the cavity, means for effecting an oscillatory rotation of one of the dies to apply an oscillatory, rotary shearing force to a sample of material held between the dies, and means for measuring a torque which is indicative of the response of the sample to the shearing force; characterised in that at least one of the dies has passageways through it which permit the passage of cooling fluid from an inlet end to an outlet and of each passageway, and the apparatus has openings to provide communication between an exterior source of cooling fluid and the inlet end of the passageways, and openings to permit discharge of the spent cooling fluid to the exterior. Preferably both dies have passageways as described, and preferably the cross-section of each passageway at its inlet end is smaller than the cross-section at its outlet end. In practice, the passageways are normally cylindrical in cross-section, and typically each passageway has a length extending from the inlet which is of relatively small uniform, diameter for example in the range 1 to 1.5 mm and which expands into a length of larger uniform diameter, for example from 1.5 to 3 mm, continuing to the outlet.

In a preferred form of die, the die has a cylindrical body with a closed end, the exterior face of the closed end being adapted to cooperate with a corresponding face of the opposing die to mould and hold the sample, and the passageways extend through the wall of the cylindrical body. Such a die is further improved by situating an integral annular flange around the open part, especially around the open end, of the cylindrical body, and having the passageways extending through the flange as well as the cylinder wall.

The cooling fluid employed is normally a gas, usually air, although for example carbon dioxide or nitrogen could be used. Pre-cooling of the gas, for example to a temperature within the range −10° to +10° C. is useful where a high rate of cooling of the dies is required.

In another aspect, the apparatus of the invention comprising two opposing, relatively-rotatable dies which are moveable between an open position and a closed position, and which are adapted, when in a closed position, to be separated by a gap and to hold between them a sample under pressure in a cavity defined by the opposing faces of the dies and a peripheral seal, means for heating the dies, means for controlling the temperature of the dies, means for sensing the temperature of the dies, means for sensing the pressure in the cavity, means for effecting an oscillatory rotation of one of the dies to apply an oscillatory rotatory shearing shearing force to a sample of material in the cavity, means for measuring a torque which is indicative of the response of the sample to the shearing force, and means for limiting the maximum size of the said gap; characterised in that the apparatus includes compensation means for urging further closure of the dies in response to a fall in the pressure on the cavity below a predetermined minimum, thus reducing the size of the gap and maintaining effective contact between the dies and the sample.

In one form of this apparatus, the die through which the oscillatory rotary shearing force is applied to the sample is mounted at one end of a coaxial drive shaft which is rotatable and slideable within a drive shaft housing. The drive shaft and housing are designed to include means to prevent sliding displacement of the drive shaft beyond a position corresponding to a maximum die gap. The compensation means also acts through the drive shaft in this form of apparatus. For example, the drive shaft can extend beyond its housing and bear on a piston rod and piston operable as parts of a pneumatic or hydraulic cylinder. The pneumatic or hydraulic pressure in the cylinder can be set at a level such that when the pressure in the sample cavity falls below a predetermined value, the drive shaft, and with it the die mounted on the drive shaft, is urged towards the other die. In an alternative system, the controlled and partial rotation of a cam in engagement with a suitable element of the drive shaft can be used for effecting the desired displacement of the drive shaft and die towards the other die. The predetermined minimum value of the cavity pressure to which the compensation means respond will vary according to the particular material under test, but is usually in the range 100–500 psi.

In addition to its use in the method of the invention, the apparatus which includes the compensation means can be used for tests on sponge compounds. For such tests, a sample of sponge compound containing a blowing agent and having a volume less than that of the die cavity is placed in the test position and the dies and housings are closed. The dies are heated to the required temperature and the compensation means are set to provide a preset constant, relatively low, pressure in the cavity. The pressure transducer will register this pressure as soon as the dies are fully closed. Torque and pressure readings taken after activation of the blowing agent can be interpreted to give information on the behaviour of the foam during its expansion.

BRIEF DESCRIPTION OF THE DRAWINGS

In the drawings, FIG. 2 shows upper and lower die assemblies, the lower die assembly being partly sectioned, together with a section on part of the drive mechanism for the lower die. FIG. 3 is a section on a,larger scale of the upper and part of the lower die assemblies.

Referring to FIG. 2, the upper and lower die assemblies, generally denoted by (1) and (2) respectively, are mounted in a framework generally similar to that described with reference to FIG. 1 of U.S. patent application Ser. No. 4552025. The casing (3) of the lower die housing is fixed to the top of a horizontal frame member (4). Rigidly inserted into the horizontal frame member (4) and extending below it is a bearing housing (5) within which a hollow drive shaft (6) is rotatable. In the arrangement shown, a radial bearing (7) is located between the drive shaft (6) near its upper end and the housing (5) at its upper end, and a radial bearing (8) is located between a lower part of the drive shaft (6) and a locknut (9). The latter has an external thread engaging with a corresponding internal thread in the lower interior face of the housing (5), so that its position relative to the housing (5) can be adjusted. A locking screw (10) is used to secure the locknut (9) in an adjusted position. An abutment projecting from the inner face of locknut (9) supports a thrust bearing (11), and a spacer (12) extends between the thrust bearing (11) and the lower face of the inner raceway of radial bearing (7). Towards its upper end, the drive shaft (6) is formed with a shoulder (13) which abuts to the upper face of the inner raceway of radial bearing (7), and at its upper open end with an integral annular drive plate (14). This in turn is fixed to an annular mounting flange (15) which carries an inner insulating ring (16). In the arrangement described, it will be seen that the interior of the hollow drive shaft (6) is open, through the mounting flange (15) to a cavity (17) which has the inner insulating ring (16) as its wall. This and other components within the lower die housing are described below with reference to FIG. 3 of the drawings.

Figure 1:
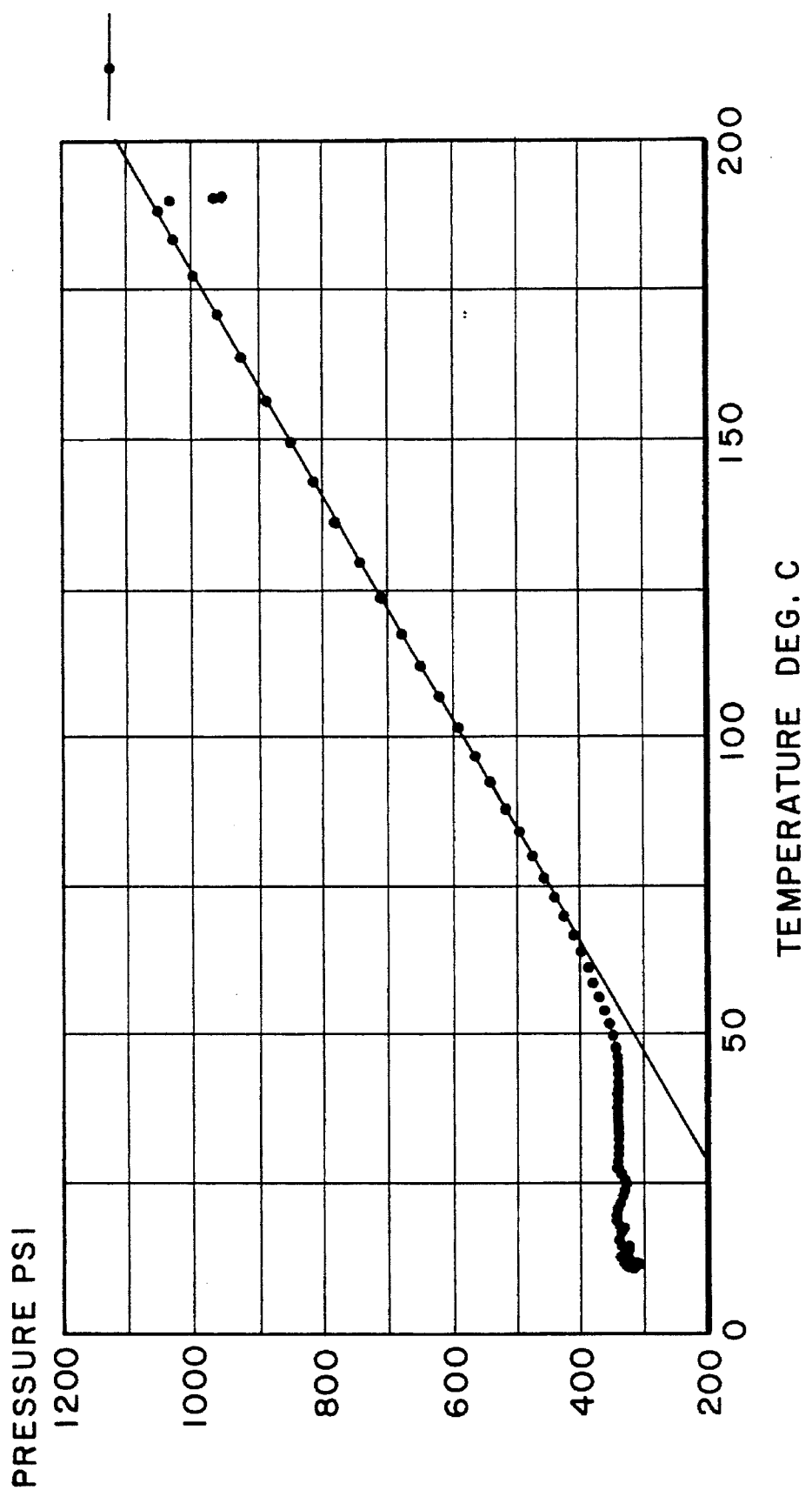
FIG. 1 is a graph showing a relationship between temperature and pressure according to the invention.

Towards its lower closed end, the drive shaft (6) is provided with a tubular side arm (18) which opens into the hollow interior of the drive shaft. At its closed end, the drive shaft bears on to a piston rod (19) and piston (20) which are components of an air cylinder (21). The air cylinder (21) is mounted on a plate (22) attached to the lower ends of rods

(23) which at their upper ends are fixed to the horizontal frame member (4). The numeral (24) indicates part of a drive arm through which an oscillatory motion can be imparted to the drive shaft (6) from a drive motor, gearbox and eccentric (not shown).

Figure 2:
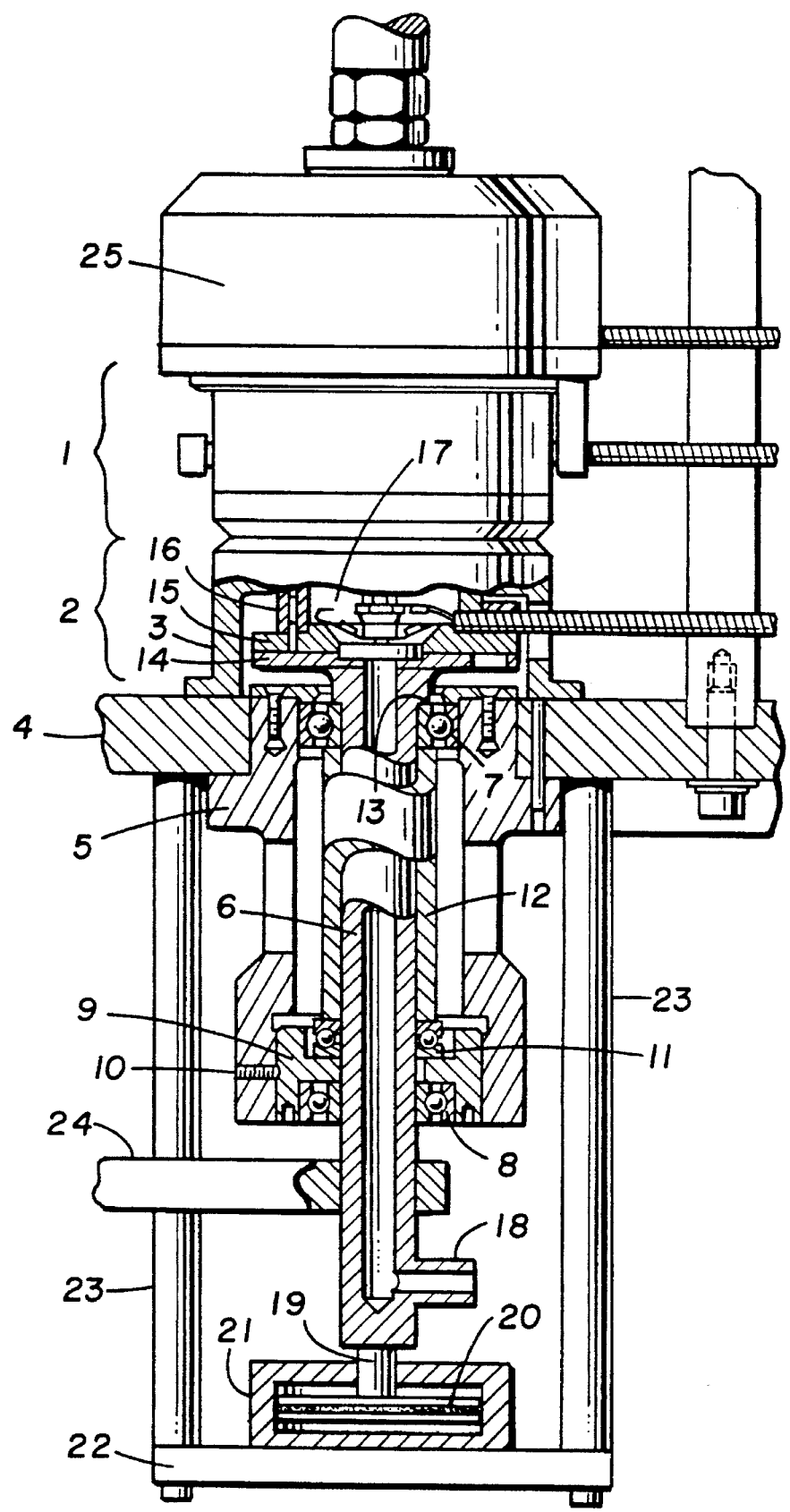
FIG. 2 shows an embodiment of the invention.
Figure 3:
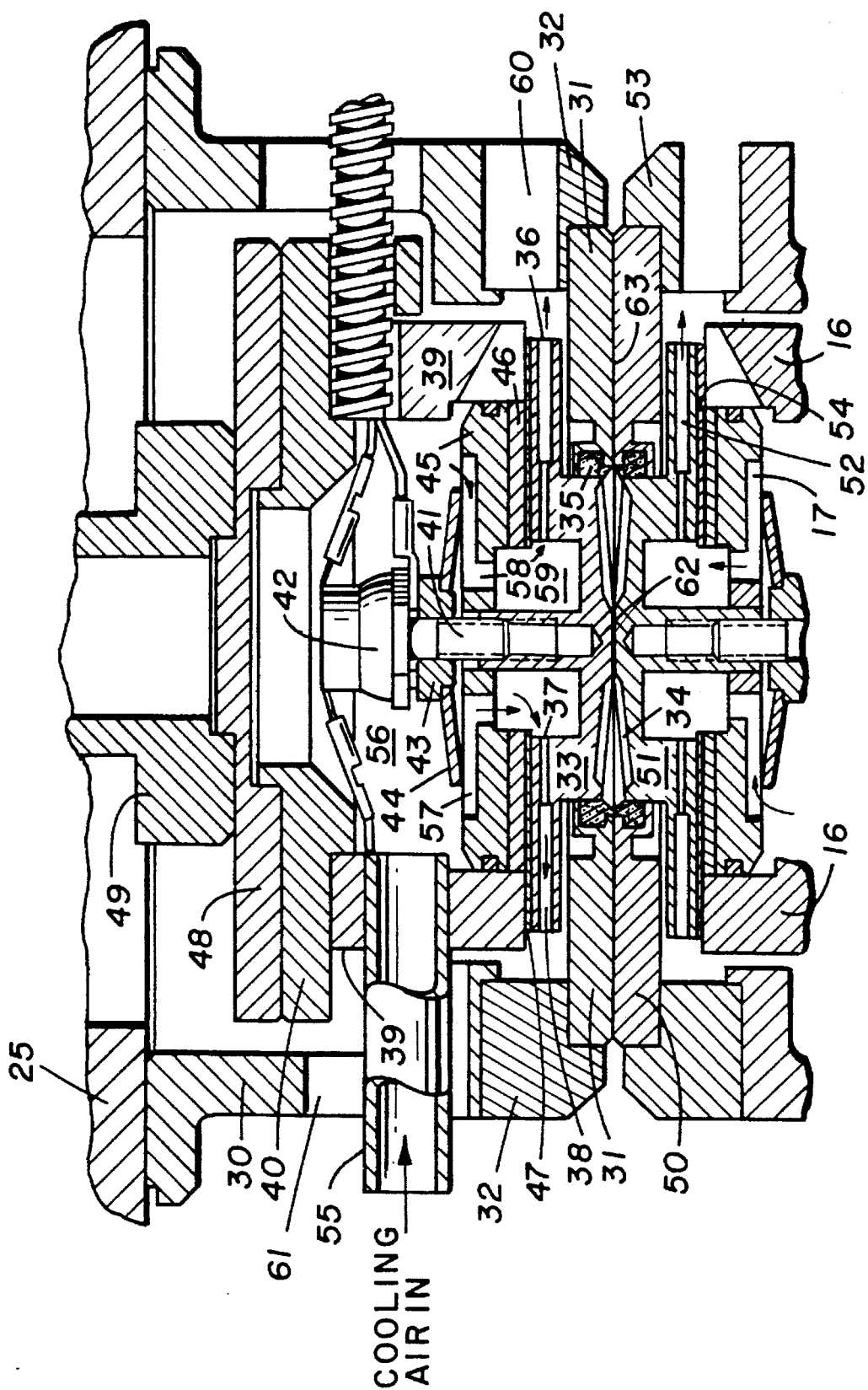
FIG. 3 is a close-up cut-away view of the upper portion of FIG. 2, and the upper and lower die assemblies in particular.

Referring to FIG. 3, the upper die housing comprises a casing (30), (which is attached to the underside of an upper casing (25) also shown in FIG. 2), a seal plate (31) and an outer insulator ring (32) through which the seal plate (31) and the casing (30) are connected. The upper die (33) has the form of a flanged, closed-end cylinder, the lower face of the end being shaped as a wide-angle truncated cone with radial grooves (34). A sealing ring (35) is located between the die (33) and the seal plate (31). The flange portion (36) of the upper die (33) has several radial passageways from the inner edge to the outer edge of the flange (36), each passageway having a small diameter inner length (37) and a larger diameter outer length (38). Other components of the upper die assembly shown in FIG. 3 include an inner insulator ring (39), through which the die is attached at its flange portion (36) to a die-mounting flange (40). A screw (41) having a thermostatic switch (42) at its head, holds a spring retainer (43) and a spring washer (44) on a retainer plate (45), all of which, together with an insulator disc (46) hold a heating element (47) in contact with the upper surfaces of the flange portion (36) of the die (33). The die-mounting flange (40) is fixed to an adaptor plate (48) having a central boss which rigidly engages with the lower end of a torque and pressure transducer (49). At its upper end (not shown) the torque transducer (49) is rigidly coupled to the top of the upper casing (25) (also shown in FIG. 2).

FIG. 3 also shows in section the upper portion of the lower die assembly, the components essentially duplicate those of the lower portion of the upper die assembly, and include a lower seal plate (50), the die (51) having passageways (52), an outer insulator ring (53) and a heater element (54).

Further notable features of the upper die assembly illustrated in FIG. 3 are the duct (55) which is bonded and sealed at its inner end into the inner insulator ring (39), and which provides the means of introducing a cooling fluid, usually air, into the cavity (56); the provision in the upper surface of the retainer plate (45) of channels (57) which terminate in ports (58) giving access from the cavity (56) through an annular chamber (59) to the inner openings of the passageways (37, 38); and the provision of openings (60) and (61) in the outer insulator ring (32) and in the casing (30) respectively, through which cooling fluid can be discharged. The direction of flow of cooling fluid through the system is indicated by arrows in the drawing. Similarly, with reference to the lower die assembly, cooling fluid introduced through the side arm (18) of the hollow drive shaft (6) (FIG. 2) enters the cavity (17). Its route through the die and other components of the lower die assembly is again indicated by the arrows in the drawing of FIG. 3.

Before using the instrument, the position of the lower die (51) relative to the seal plate (50) is adjusted by means of locknut (9) so that in the closed position illustrated in FIG. 3, and in the absence of a sample, the seal plates (31) and (50) are in abutment, but there remains a gap (62) of predetermined size between the centre of the dies. In a typical test of a rubber or rubber-like material, a sample of material is placed on the heated lower die (51) with the dies in the open position. The volume of the sample is slightly greater than that of the cavity formed between the closed dies, so that as the upper die (33) is forced into the closed position, the material is moulded to fill the die cavity and excess material is extruded radially between the dies and seal plates until a peripheral seal of material is formed in the region (63) at the inner edges of the seal plates (31) and (50). Initially the gap (62) will increase as the pressure in the die cavity is transmitted through the components of the lower die assembly, the shoulder (13) of the drive shaft (6), the inner raceway of radial bearing (7), the spacer (12), the thrust bearing (11) and the abutment of locknut (9) until a position of maximum displacement is reached. The actual displacement during this time is very small, and represents the eliminate of 'play' between the components, and a small amount of elastic compression of the thrust bearing (11). In any given instance, the actual displacement will also depend on the stiffness of the sample and on the force used in closing the dies. Any reduction in the pressure in the die cavity, for example during cooling or caused by shrinkage of the sample during vulcanisation, will result initially in the elastic recovery of the thrust bearing (11). Thereafter, however, continued reduction in pressure could result (in the prior art instrument where the predetermined gap represents the minimum separation of the dies) in loss of fully effective contact between the dies and the sample (ie. slippage). In the apparatus of the present invention shown in FIG. 2, air pressure is applied to the underside of piston (20) at a compensation pressure above the critical cavity pressure at which otherwise slippage would occur. As soon as the pressure in the cavity falls below the compensation pressure, the drive shaft (6) and its associated components including the lower die (51) are raised, and effective contact between the dies and sample is maintained.

Figure 4:
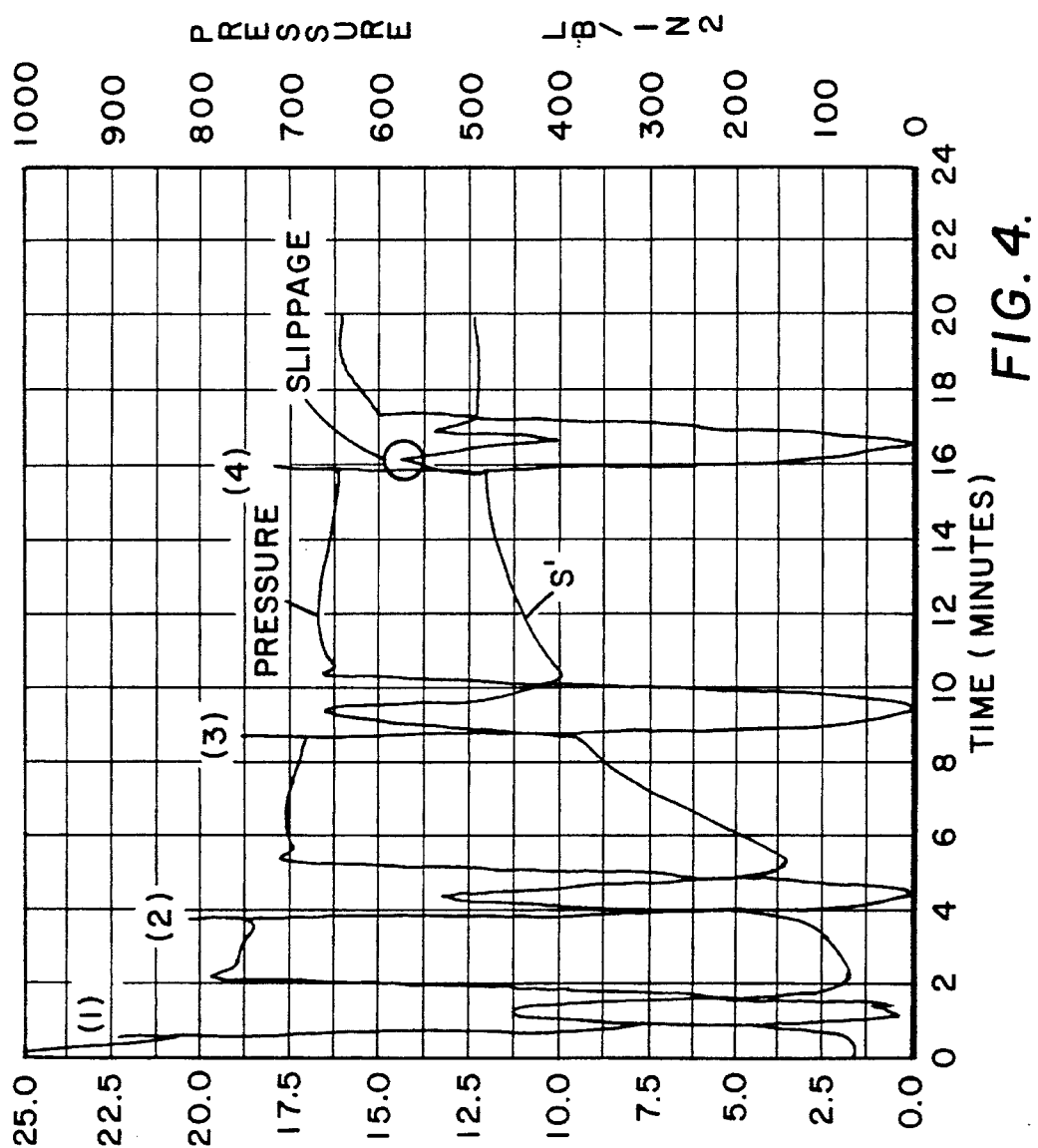
FIG. 4 is a graph of pressure versus time for a sample of a compounded SBR stock tested according to the invention.

Typical torque and pressure versus time curves for a sample of a compounded SBR stock tested according to the method of the invention, but without pressure compensation for shrinkage of the sample, are shown in FIG. 4 of the drawings. Each pressure drop corresponds to a fall in the temperature of the dies and sample from 170° C. to about 30° C., and each pressure increase accompanies reheating to 170° C. It will be noted that the value of S' during successive cooling periods progressively increases until the fourth such period. The erratic values of S' during the cooling and reheating period between 16 and 17 minutes indicate slippage between the dies and the sample. Curves such as those shown in FIG. 4 are characteristic of the elastomer stock under test, and can be used to distinguish between different stocks.

Figure 5A:
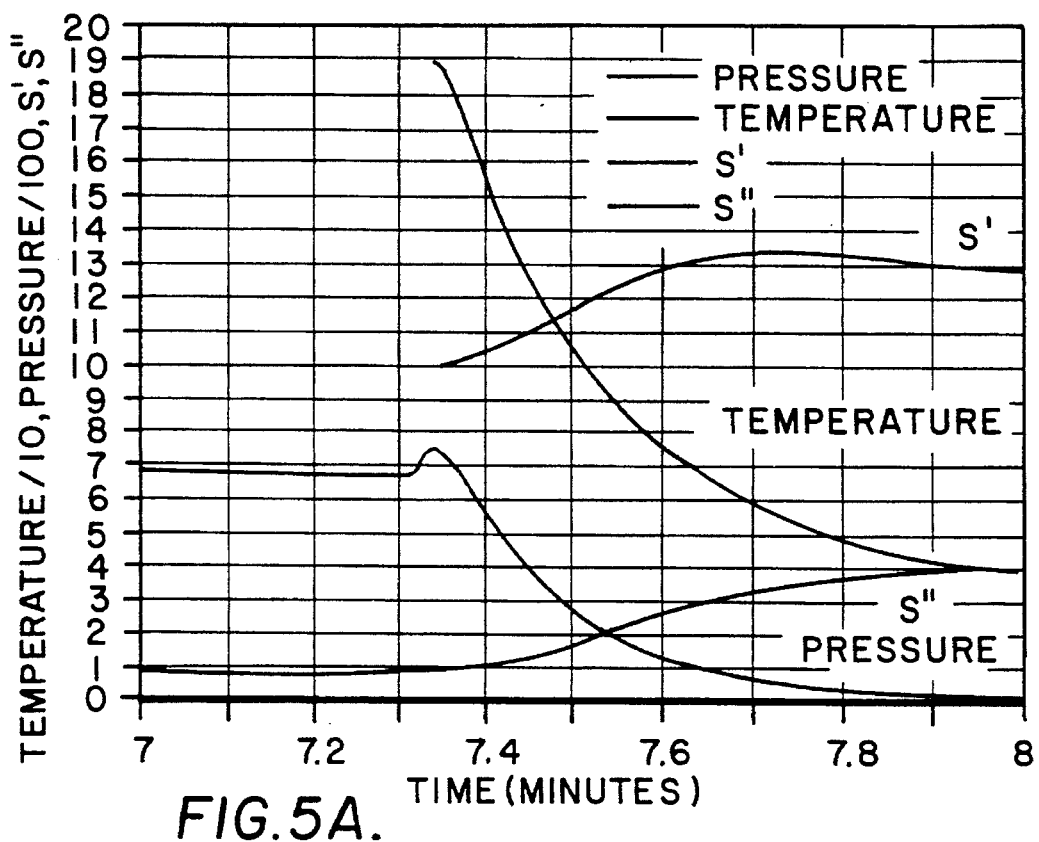
FIGS. 5A and 5B are graphs of data obtained during post-vulcanisation cooling.
Figure 5B:
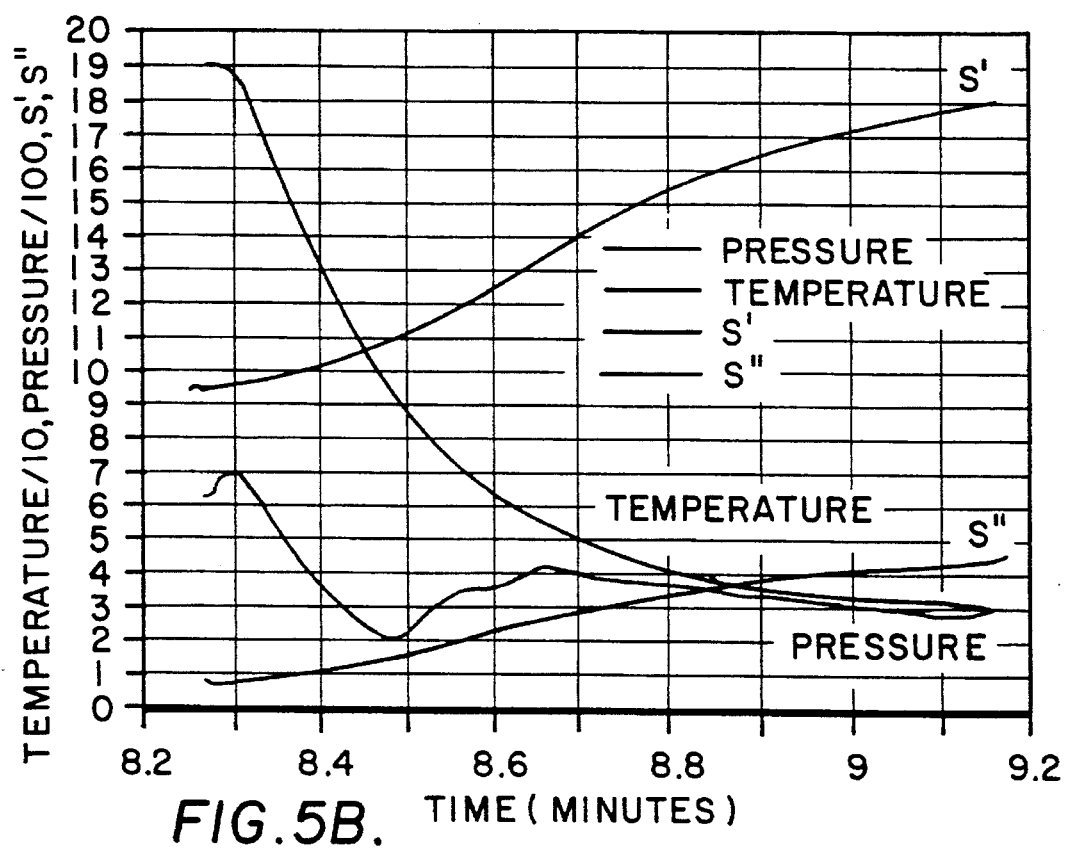

FIGS. 5A and 5B show the data obtained during the final (post-vulcanisation) cooling in a multi-cool/reheat test similar to that illustrated in FIG. 4 but with a top (vulcanisation) temperature of 190° C. The test procedure which generated the data of FIG. 5A did not include die pressure compensation for shrinkage so that after the start of cooling just after 7.3 minutes, there is a continual fall in pressure.

The value of S' rises to a maximum and then decreases. This behaviour is indicative of slippage between the sample and the dies, and is to be contrasted with that shown in FIG. 5B. For the latter case, the test procedure included using the pressure compensation device to prevent the pressure in the die cavity falling below a predetermined minimum. The result was a continuous increase in the value of S', in line with expectations.

Figure 6A:
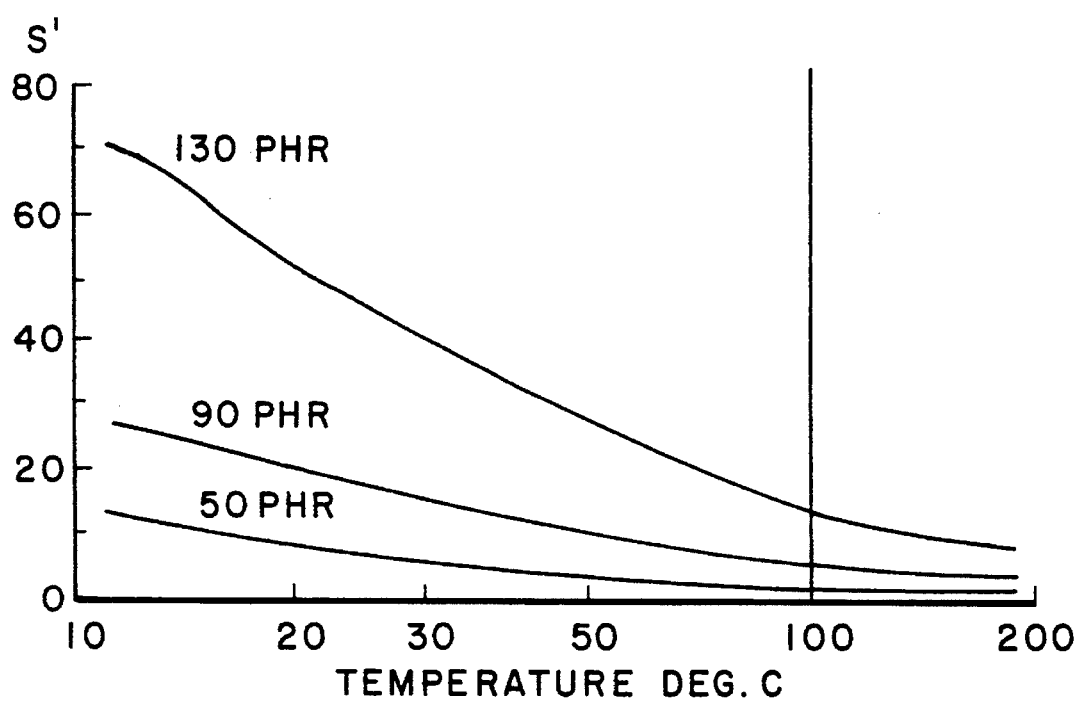
FIGS. 6A and 6B illustrate the effect of different levels of N330 carbon black filler.
Figure 6B:
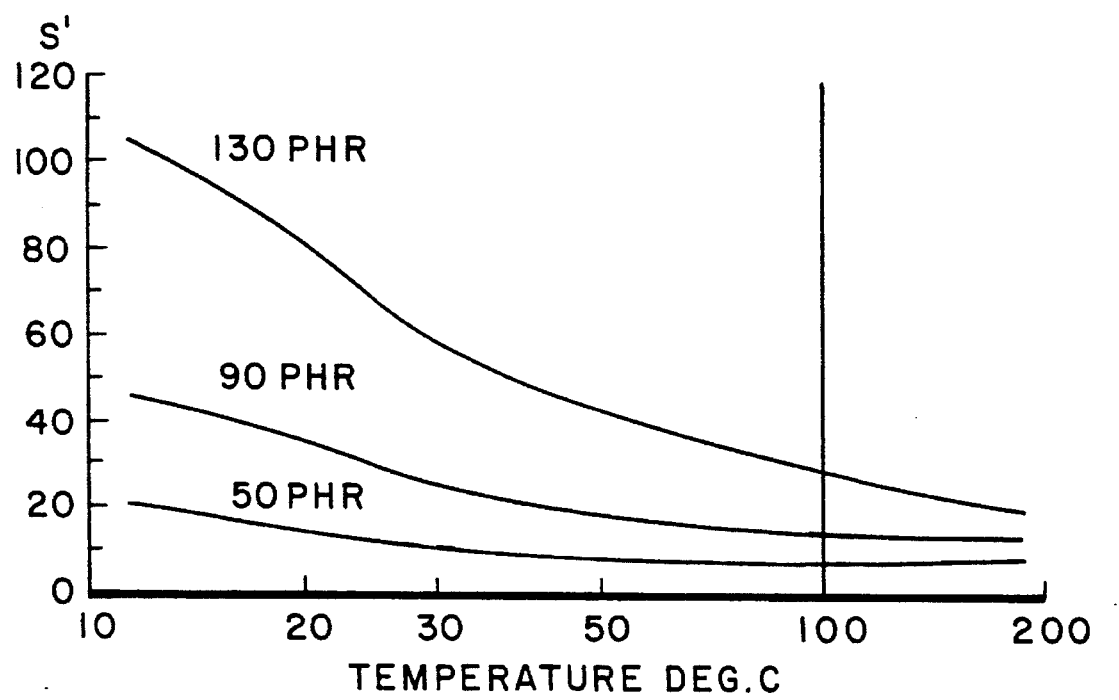

FIGS. 6A and 6B show data obtained in a study of the effect of different levels of N330 carbon black filler, namely 50, 90 and 130 phr, in a vulcanisable SBR stock. The test procedure involved loading the sample and closing the dies (die temperature 190° C.), switching the cooling on and monitoring torque and temperature during cooling to about 12° C. The results are shown in FIG. 6A. The heating was then switched on again to reheat the sample to 190° C. This temperature was maintained until the sample was fully cured as indicated by a steady value of S', with the pressure compensation device operative to arrest the fall in pressure at 330 psi. The dies and sample were then cooled, and the torque and temperature monitored. The results on the same three SBR stocks are shown in FIG. 6B. The S'/temperature curves of FIGS. 6A and 6B show that both before and after curing, the value of S' is significantly more sensitive to the level of carbon black at lower temperatures. The value of the method of the invention in providing differentiation such as this is therefore apparent.

Figure 7:
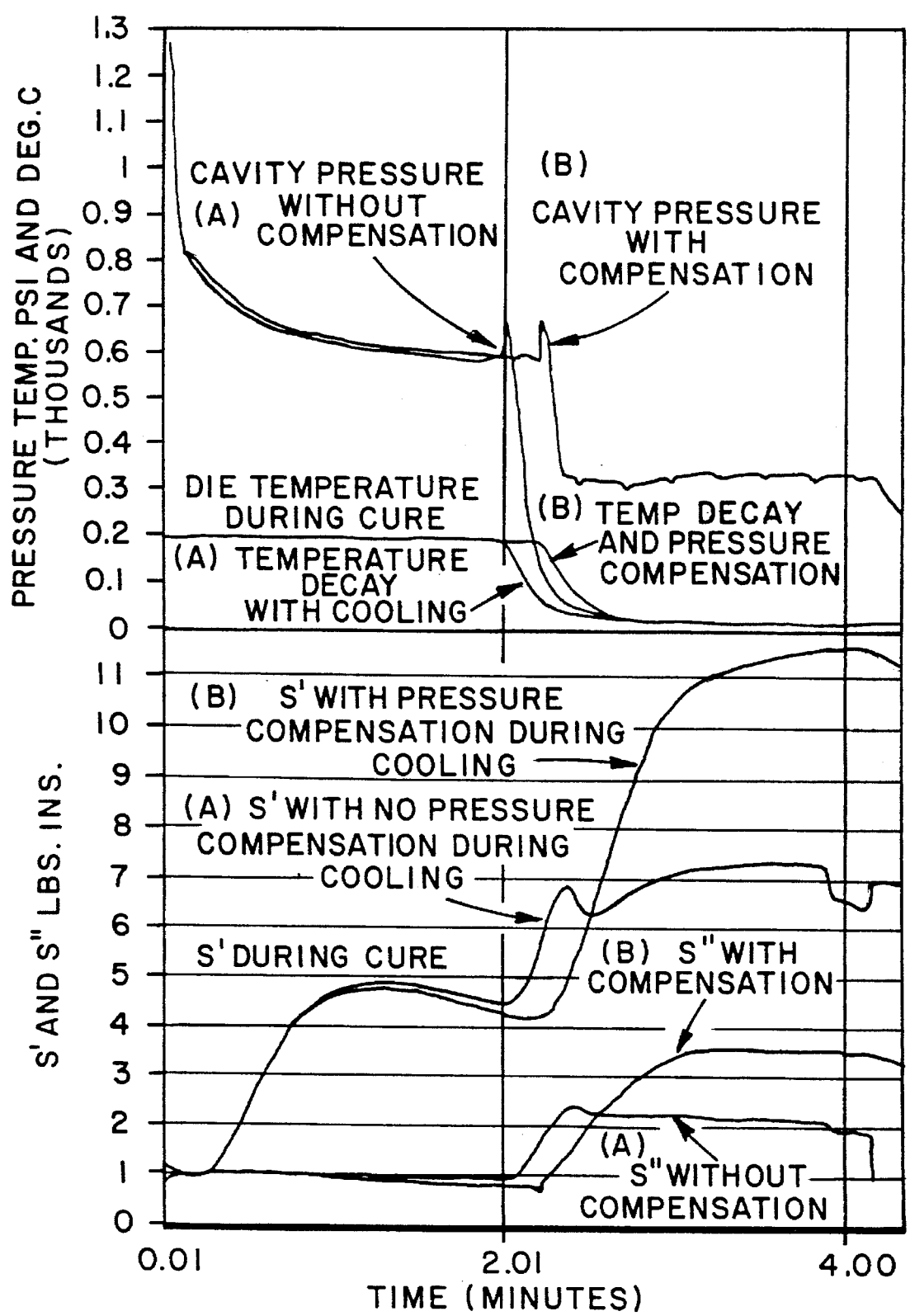
FIG. 7 shows the results of placing a polyester film between each die and the sample.

FIG. 7 shows results obtained in tests where a 0.023 mm thick polyester film was placed between each die and the sample. The sample was a natural rubber compound cured at 190° C. and which was rapidly cooled after cure. The series of graphs (A) indicate the effect on torque (S' and S") caused by slippage as the cavity pressure decays below a critical threshold during cooling. Series (B) indicates how slippage is prevented by the pressure compensation system which allows the torque values (S' and S") to continuously increase as expected in the absence of slippage.

We claim:

1. A method for the characterisation of viscoelastic materials in which a sample of material is held under measured pressure and temperature between two opposed, temperature-controlled dies and in which the sample is subjected to an oscillatory, rotary shearing force by osciliatory rotation of one of said dies relative to the other, and a torque which is indicative of the response of the sample to the shearing force is measured, characterised in that at least once during its residence between the dies the sample is (i) cooled at an average rate of cooling of at least 1° C. per second and, if necessary, the resultant pressure drop is limited to avoid slippage between the sample and the dies, and (ii) reheated, and information on the characteristics of the sample is derived from the torque measurements at least during the period or periods of cooling.

2. A method according to any of claim 1 in which the sample is cooled to 30° C. or below.

3. A method according to any of claim 1 in which the average rate of reheating is at least 1° C. per second.

4. A method according to any of claim 1 in which the material is a vulcanisable elastomer composition and the sample is cooled at least once before the onset of vulcanisation, and after vulcanisation is complete.

5. A method according to any of claim 1 in which the torque values are corrected in response to changes in the gap between the dies.

6. Apparatus for testing a sample of viscoelastic material comprising two opposing, relatively rotatable dies, which are moveable between an open position and a closed position, and which are adapted when in a closed position, to be separated by a gap and to hold between them a sample under pressure in a cavity defined by the opposing faces of the dies and a peripheral seal, means for heating the dies, means for cooling the dies, means for sensing the temperature of the dies, means for sensing the pressure in the cavity, means for effecting an oscillatory rotation of one of the dies to apply an oscillatory rotary shearing force to a sample of material held between the dies, and means for measuring a torque which is indicative of the response of the sample to the shearing force; characterised in that at least one of the dies has passageways through it which permit the passage of cooling fluid from an inlet end to an outlet end of each passageway, and the apparatus is provided with openings to provide communication between an exterior source of cooling fluid and the inlet ends of the passageways and openings to permit discharge of the spent cooling fluid to the exterior.

7. Apparatus according to claim 6 in which each passageway has a length at the inlet end of relatively small cross-section and a length at the outlet end of relatively larger cross-section.

8. Apparatus according to either claim 6 or claim 7 in which the said at least one die has a cylindrical body having a closed end, the exterior face of which end is adapted to cooperate with a corresponding face of the opposing die to mold and hold the sample, and the passageways are passageways through the cylindrical body wall.

9. Apparatus according to claim 8 in which the die has an integral annular flange surrounding the open end of the cylindrical body, and the passageways extend through the cylinder body wall and through the flange.

10. Apparatus for testing a sample of viscoelastic material comprising two opposing, relatively-rotatable dies which are moveable between an open position and a closed position, and which are adapted, when in a closed position, to be separated by a gap and to hold between them a sample under pressure in a cavity defined by the opposing faces of the dies and a peripheral seal, means for heating the dies, means for controlling the temperature of the dies, means for sensing the temperature of the dies, means for sensing the pressure in the cavity, means for effecting an oscillatory rotation of one of the dies to apply an oscillatory rotary shearing force to a sample of material in the cavity, means for measuring a torque which is indicative of the response of the sample to the shearing force, and means for limiting the maximum size of the said gap, characterised in that the apparatus includes compensation means for urging further closure of the dies in response to a fall in the pressure in the cavity below a predetermined minimum, thus reducing the size of the gap and maintaining effective contact between the dies and the sample.

11. Apparatus according to claim 10, wherein the die through which the oscillatory rotary shearing force is applied to the sample is mounted at one end of a drive shaft, and the compensation means acts through the said drive shaft.

* * * * *